United States Patent [19]

Youssefyeh et al.

[11] Patent Number: 4,839,369

[45] Date of Patent: Jun. 13, 1989

[54] ARYL AND HETEROARYL ETHERS AS AGENTS FOR THE TREATMENT OF HYPERSENSITIVE AILMENTS

[75] Inventors: Raymond Youssefyeh, Tarrytown; Utpal Chakraborty, Bedford Hills; Ernest Magnien, Flushing; Rohit Desai, Millwood, all of N.Y.

[73] Assignee: Rorer Pharmaceutical Corporation, Fort Washington, Pa.

[21] Appl. No.: 839,410

[22] Filed: Mar. 13, 1986

Related U.S. Application Data

[63] Continuation of Ser. No. 723,781, Apr. 16, 1985, abandoned.

[51] Int. Cl.$^4$ .................... A61K 31/47; C07D 215/00
[52] U.S. Cl. ..................................... 514/314; 546/152
[58] Field of Search ......................... 514/314; 546/152

[56] References Cited

U.S. PATENT DOCUMENTS

| 4,244,956 | 1/1981 | Dewhirst | 548/329 |
| 4,567,184 | 1/1986 | Musser et al. | 514/277 |
| 4,661,499 | 4/1987 | Young et al. | 514/311 |

FOREIGN PATENT DOCUMENTS

| 0181568 | 5/1986 | Fed. Rep. of Germany . |
| 0189142 | 7/1986 | Fed. Rep. of Germany . |
| 0110405 | 9/1986 | Netherlands . |
| 0190722 | 5/1987 | Netherlands . |
| 86105287 | 12/1988 | Netherlands . |

*Primary Examiner*—Stanley J. Friedman

[57] ABSTRACT

Aryl and Heteroaryl Ethers are used for their anti-inflammatory and anti-allergic properties.

17 Claims, No Drawings

ARYL AND HETEROARYL ETHERS AS AGENTS FOR THE TREATMENT OF HYPERSENSITIVE AILMENTS

This application is a continuation of U.S. application Ser. No. 723,781 filed Apr. 16, 1985 now abandoned.

This invention relates to the use of certain chemical compounds possessing valuable pharmaceutical activity, particularly as lipoxygenase inhibitors possessing anti-inflammatory and anti-allergic properties.

SUMMARY OF THE INVENTION

A therapeutic composition comprising as an active ingredient a compound of the formula

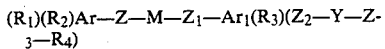

and salts thereof; wherein.
Ar and $Ar_1$ are independently phenyl, naphthyl or a nitrogen, oxygen, or sulfur heterocyclic ring;
$R_1$, $R_2$, $R_3$ and $R_4$ are independently H, lower alkyl, lower alkoxy, hydroxy, halo, trihalomethyl, hydroxy-lower alkyl, alkyl carboxy, carboxy, formyl, lower alkyl carbonyl, aryl, aryloxy, benzyloxy, lower alkylamino, diloweralkylamino, cyano, lower alkanoyloxy, carbamoyl, lower alkoxy-lower alkoxy, lower carbalkoxy-lower alkoxy, nitro, amino, tetrahydropyranylmethyl, or tetrazole, or tetrazole lower alkyl;
$R_4$ can additionally be $R_5$;
$R_5$ is lower alkoxy, phenyl, OH, $CO_2R_6$,

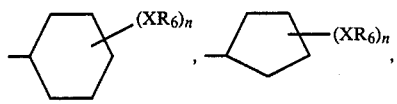

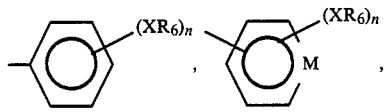

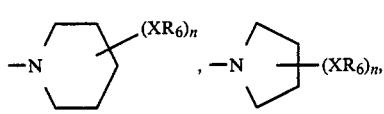

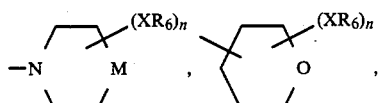

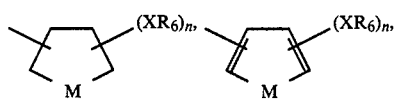

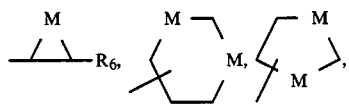

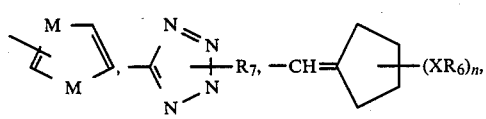

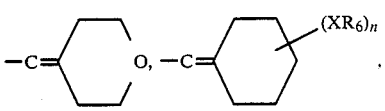

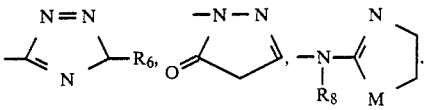

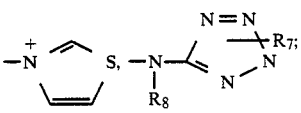

$R_6$ is H, lower alkyl, aryl, or lower aralkyl;
$R_7$ is H, lower alkyl,

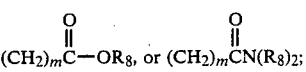

$R_8$ is H or lower alkyl;
each M is independently O, S, or $NR_8$;
m is 0 to 5;
n is 0 or 1;
X is O, S, $NR_8$;
Z, $Z_1$, $Z_2$ and $Z_3$ are independently a chemical bond or an alkylene chain containing up to 5 carbon atoms in the principal chain and up to a total of 8 carbon atoms;
Y is a chemical bond, O, S, NR, CO, $CHOR_8$, CH=CH, $CH_2$—CH=CH, COO—, or $CH_2$; with the proviso that when Y is O, S, or $NR_8$, $R_4$ is not OH or $CO_2R_6$.
Preferred are compounds of the formula

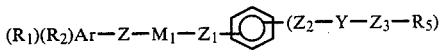

and salts thereof, wherein
Ar is phenyl, napthyl, quinoline or isoquinoline;
$R_1$ and $R_2$ are each independently H, lower alkyl, lower alkoxy, hodroxy, halo, trihalomethyl, hydroxy-lower alkyl, carboxy, formyl, phenyl, phenoxy, benzyloxy, loweralkylamino, di-loweralkylamino, cyano, lower alkanoyloxy, carbamoyl, lower alkoxy-lower alkoxy, lower carbalkoxy-lower alkoxy, or

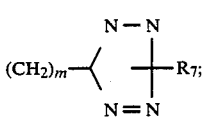

Z, $Z_1$, $Z_2$ and $Z_3$ are independently a chemical bond or an alkylene chain containing up to 5 carbon atoms in the principal chain and up to a total of 8 carbon atoms;
M is O, S, or $NR_8$;
Y is a chemical bond, O, or $CHOR_8$;
$R_5$ is lower alkoxy, phenyl, OH, $CO_2R_6$,

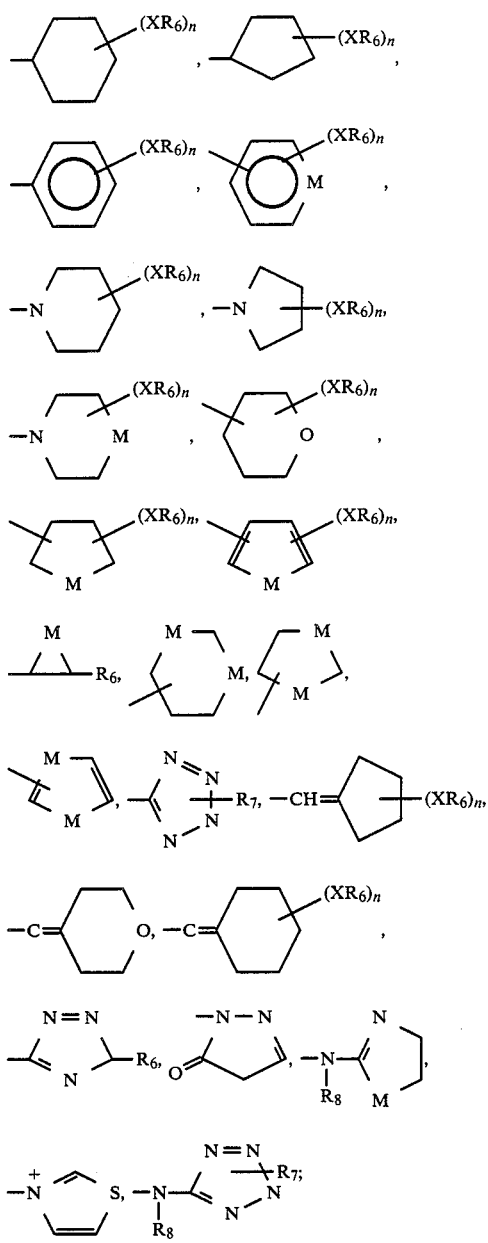

$R_6$ is H, lower alkyl, phenyl, or phenyl-lower alkyl;
$R_7$ is H, lower alkyl,

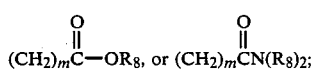

$R_8$ is H or lower alkyl;
each M is independently O, S, or $NR_8$;
m is 0 to 5;
n is 0 or 1;
X is O, S, $NR_8$;
Z, $Z_1$, $Z_2$, and $Z_3$ are independently a chemical bond or an alkylene chain containing up to 5 carbon atoms in the principal chain and up to a total of 8 carbon atoms;
Y is a chemical bond, O, S, NR, CO, $CHOR_8$, CH=CH, $CH_2$—CH=CH, COO—, or $CH_2$; with the proviso that when Y is O, S, or $NR_8$, $R_4$ is not OH or $CO_2R_6$.

Even more preferred are compounds of the structure

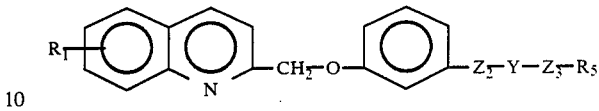

and salts thereof, wherein
$R_1$ is H, $C_{1-5}$ alkyl, $OR_8$, halo $CF_3$,

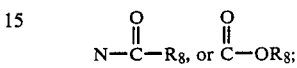

$R_8$ is H or lower alkyl;
$Z_2$ is a chemical bond or $(CH_2)_m$;
$Z_3$ is a chemical bond or $(CH_2)_m$;
m is 0-5;
Y is a chemical bond, —O—, or

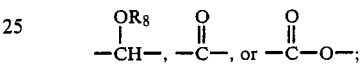

$R_5$ is $C_{1-10}$ alkyl, $OR_8$,

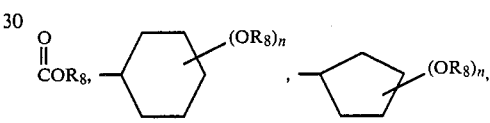

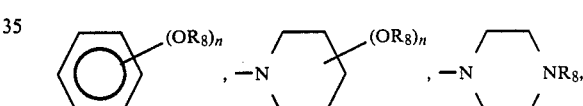

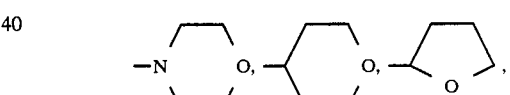

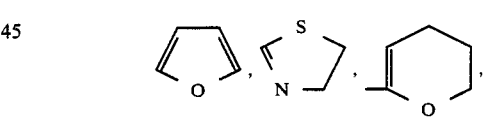

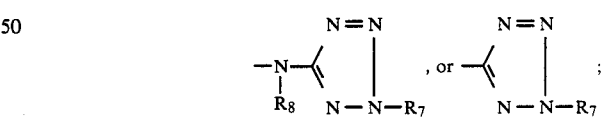

$R_7$ is H, lower alkyl, or

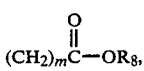

and
n is 0 or 1.

In addition, the present invention relates to the method of using these compounds as lipogenase inhibitors possessing anti-inflammatory and anti-allergic responses.

The heterocyclic rings exemplary of Ar and $Ar_1$ contain at least one oxygen, sulfur or nitrogen and include the so-called benzoheterocyclic rings. Exemplary heterocyclics include furan, thiophene, pyrrole, pyridine, thiazole, piperazine, oxazole, benzofuran, quinoline, isoquinoline, indole, benzothiophene, benzoxazole and similar heterocyclic rings as well as the N-oxides of the nitrogen-heterocyclics. The preferred heterocyclic is quinoline.

The alkyl groups, either alone or within the various substituents, defined hereinbefore, are preferably lower alkyl, which may be straight or branched chain and include methyl, ethyl, propyl, isopropyl, butyl, isobutyl, amyl, hexyl and the like. Preferable lower alkyl contain 1 to 6 carbon atoms.

The halo atoms in halo and trihalomethyl are Cl, Br, I and preferably F. The aryl groups are preferably phenyl.

The preferred compounds are those in which the alkylene chain represented by Z contains from 0 to 3 carbon atoms and is a normal alkylene chain, most preferably unsubstituted, Ar is quinoline, $Ar_1$ is phenyl and M is O. Of the substituents on Z, the preferred are lower alkyl, e.g., methyl, ethyl and isopropyl.

The present compounds can be prepared by art-recognized procedures from known compounds or readily preparable intermediates. An exemplary general procedure is as follows:

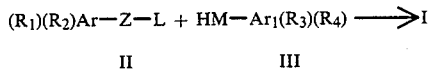

wherein
$R_1$, $R_2$, Ar, Z, M, $Ar_1$, and $R_3$ and $R_4$ are as defined above, and L is a leaving group, such as halo, tosylate, or mesylate.

If M is O or S, any base normally employed to deprotonate an alcohol or thiol may be used, such as sodium hydride, sodium hydroxide, triethyl amine, sodium bicarbonate or diisopropyl/ethylamine.

The above bases may also be used when M is an amine. Reaction temperatures are in the range of room temperature to reflux and reaction times vary from 2 to 48 hours. The reaction is carried out in a solvent that will dissolve both reactants and is inert to both as well. Solvents include, but are not limited to, diethyl, ether, tetrahydrofuran, N,N-dimethyl formamide, dimethyl sulfoxide, dioxane and the like.

As a further variation, the amino derivatives can be prepared by condensation of an aldehyde

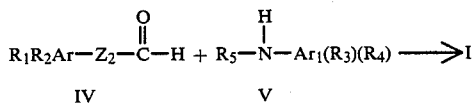

(IV) with a primary amine (V) to form the corresponding imine and the imine is reduced to give a compound of Formula I wherein M is nitrogen and $R_5$ is hydrogen. This product can be alkylated with alkylating agents known in the art, such as alkyl iodides, to form compounds of Formula I wherein M is nitrogen and $R_5$ is lower alkyl. In this process $R_1$, $R_2$, $R_3$, $R_4$, $R_5$, Ar and $Ar_1$ are as defined hereinabove and $Z_2$ is an alkylene chain containing 0 to 4 carbon atoms.

The aforementioned condensation reaction to form imines with subsequent hydrogenation can be conveniently carried out in a single reaction zone by the expediency of mixing the aldehyde (IV) with the amine (V) under hydrogenation conditions. For practical purposes, the aforesaid reactants can be hydrogenated over noble metal catalysts such as palladium over platinum, rhodium, ruthenium, and the like, and the two stages occur under such conditions to produce the desired end products. Alternatively, the imine can be reduced with Lewis acids, such as $NaBH_3CN$, sodium borohydride and the like under the above conditions.

As in any organic reaction, solvents can be employed, such as methanol, methylene chloride, chloroform, tetrahydrofuran, dioxane, diethyl ether, ethanol and the like. The reaction is normally effected at or near room temperature, although temperatures from 0° C. up to the reflux temperature of the reaction mixture can be employed.

The present compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, sulfuric, nitric, benzenesulfonic, toluenesulfonic, acetic, malic, tartaric and the like which are pharmaceutically acceptable. Basic salts for pharmaceutical use are the Na, K, Ca and Mg salts.

Various substituents on the present new compounds, e.g., as defined in $R_1$, $R_2$, $R_3$, and $R_4$ can be present in the starting compounds, added to any one of the intermediates or added after formation of the final products by the known methods of substitution or conversion reactions. If the substituents themselves are reactive, then the substituents can themselves be protected according to the techniques known in the art. A variety of protecting groups known in the art may be employed. Examples of many of these possible groups may be found in "Protective Groups in Organic Synthesis" by T. W. Green, John Wiley and Sons, 1981. For example, the nitro groups can be added to the aromatic ring by nitration and the nitro group converted to other groups, such as amino by reduction, and halo by diazotization of the amino group and replacement of the diazo group. Alkanoyl groups can be substituted onto the aryl groups by Friedel-Crafts acylation. The acyl groups can then be transformed to the corresponding alkyl groups by various methods, including the Wolff-Kishner reduction and Clemmenson reduction. Amino groups can be alkylated to form mono and dialkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepithelially including transdermal, opthalmic, sublingual and buccal; topically including opthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustainedrelease preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Despersions can also be prepared in glycerol, liquid polyethylene glycols, and mixtures thereof and inoils.

Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It may be stable under the conditions of manufacture and storage and must be preserved against the contaminating action of microorganisms such as bacteria ad fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from 0.1 to 100 uM/day, or from about 0.1 mg to about 50 mg/kg of body weight per day and higher, although it may be administered in several different dosage units. Higher dosages are required for oral administration.

The following examples are illustrative.

EXAMPLE 1

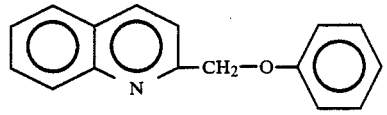

2-Phenoxymethyl quinoline

A mixture of 2-chloromethyl quinoline (0.05 mol), phenol (0.055 mol), finely powdered potassium carbonate (0.055 mol), cesium carbonate (0.055 mol) and sodium iodide (0.0025 mol) in acetone was refluxed for about 4 hours. The reaction mixture was cooled to room temperature and filtered and the filtrate was concentrated and dissolved in ether. The ether solution was washed thoroughly with 1N NaOH solution, water and brine. After drying the ether solution over anhydrous magnesium sulfate, and filtering off the drying agent, the solvent was evaporated off to leave the crude product which was crystallized from hexane and ether to yield the desired compound as a light yellow solid, m.p. 79.5°–80.5° C.

EXAMPLE 2

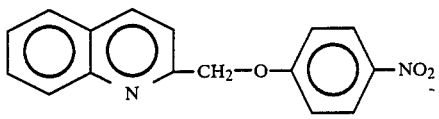

2-(p-Nitrophenoxymethyl)quinoline

This compound was prepared in an identical manner as described in Example 1, except p-nitrophenol was substituted for phenol, m.p. 142°–143° C.

EXAMPLE 3

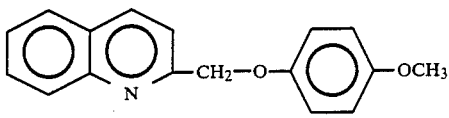

2-(p-Methoxyphenoxymethyl)quinoline

This compound was prepared in an identical manner as described in Example 1, except p-methoxyphenol was substituted for phenol, m.p. 79°–80° C.

EXAMPLE 4

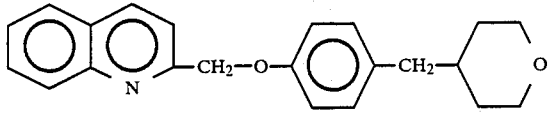

2-(4-(4-Tetrahydropyranomethyl)phenoxymethyl)-quinoline

A mixture of 2.6 g (0.013 mol) 4-(4-tetrahydropyranomethyl) phenol, 2.9 g (0.013 mol) 2-chloromethyl quinoline hydrochloride and 15 ml (2N, NaOH) in 15 ml DMF and 50 ml THF was stirred overnight at 60° C. bath temperature. The reaction mixture was poured into water and extracted with ether. The ether extract was washed with water, dried and concentrated to dryness under reduced pressure. The residue was passed through a silica gel column using hexane/ethylacetate (3:1) as eluent. Evaporation of eluent gave solid (0.7 g), m.p. 90°–92° C.

EXMPLE 5

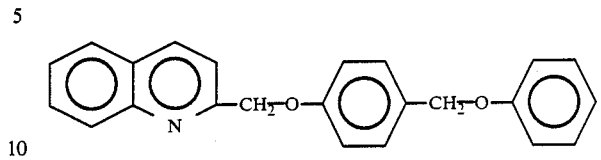

2-(4-(Phenoxymethyl)phenoxymethyl)quinoline

A mixture of 5.0 g (0.025 mol) 4-phenoxymethylphenol, 5.35 g (0.025 mol) 2-chloromethylquinoline hydrochloride and 30 ml (2N, NaOH) in 50 ml DMF and 100 ml THF was stirred at 60° C. bath temperature for a period of 3 hours. The reaction mixture was poured into wast and extracted with ether. The ether extract was washed with water, dried and concentrated to dryness to obtain solid. Recrystallization from acetonitrile yielded (2.0 g) product, m.p. 100°–111° C.

EXAMPLE 6

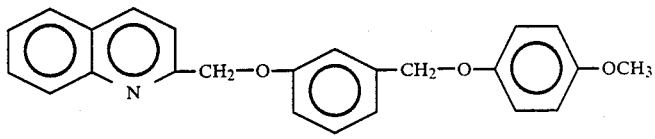

2-[3-(p-Methoxyphenoxymethyl)phenoxymethyl]-quinoline

A mixture of 1.2 g (0.01 mol) 4-methoxyphenol, 3.2 g (0.01 mol) 2-(3-chloromethylphenoxymethyl)quinoline hydrochloride,, 2.8 g (0.02 mol) potassium carbonate and 2.8 g (0.017 mol) potassium iodide in 100 ml acetone was refluxed over a period of 24 hours. Reaction mixture was concentrated to dryness and slurried into water and extracted with ether. The ether extract was washed with water, dried over MgSO4 and concentrated to dryness under reduced pressure to obtain solid. Recrystallization from isopropanol yielded 2.1 g product, m.p. 83°–85° C.

EXAMPLE 7

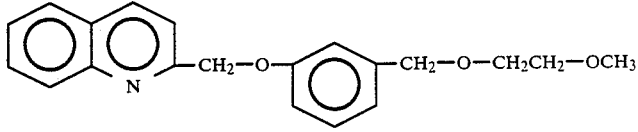

2-(3-(2-Methoxyethoxymethyl)phenoxymethyl)quinoline 1.1 g (0.015 mol) of 2-methoxyethanol was dissolved in 50 ml THF. To this solution 1.5 g (0.03 mol, 50% oil dispersion) NaH, (0.015 mol) 2-(3-chloromethylphenoxymethyl)quinoline hydrochloride, was added slowly. After the addition was completed, the mixture was heated at 70° C. bath temperature for overnight. The reaction mixture was poured into water and extracted with ether. The ether extract was washed with water, dried and concentrated to dryness under reduced pressure. The residue was passed through a silica gel col-

EXAMPLE 8

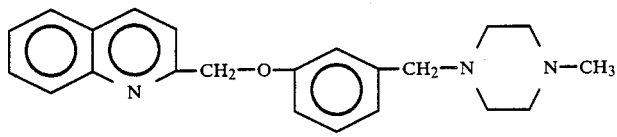

2-(3-(4-Methylpiperazin-1-ylmethyl)phenoxymethyl)-quinoline

A mixture of 4.7 g (0.015 mol) 2-(3-chloromethyl-phenoxymethyl) quinoline hydrochloride, 6 g (0.06 mol) N-methylpiperazine in 50 ml acetonitrile was heated over steam bath for a period of 8 hours. Reaction mixture was concentrated to dryness and sluried into water, and extracted with ether. The ether extract was washed with water, dried over MgSO₄ and concentrated to dryness under reduced pressure. The residue was passed through a silica gel column using acetone as eluent. Evaporation of eluent gave solid (0.6 g), m.p. 47°–49° C.

EXAMPLE 9

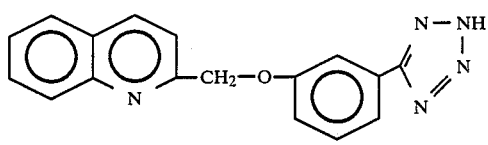

5-[3-(2-Quinolymethyloxy)phenyl]tetrazole

A mixture of 8.8 g of 3-(2-quinolylmethyloxy)benzonitrile, 2.3 g of sodium azide and 1.9 g of ammonium chloride in 100 ml of dimethylformamide was stirred at 140° C. for 7 hours. An additional amount of sodium azide (1.2 g) and ammonium chloride (1.0 g) was added and stirring resumed at 140° C. for 17 hours. The mixture was poured over ice and acidified with hydrochloric acid. The crude product solidified and was filtered off to give 11 g of crude product. The crude product was slurried with hot methanol and filtered off. To a hot solution of this material was added enough water to cause turbidity. On cooling the compound crystallized and was filtered off to yield 5.0 g of pure material having an m.p. of 200°–205° C. dec.

EXAMPLE 10

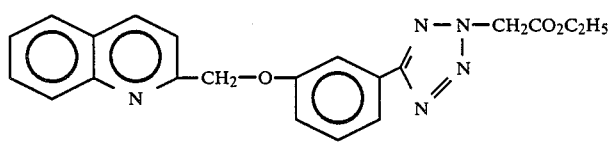

2-Carbethoxymethyl-5-[3-(2-quinolylmethyloxy)-phenyl]tetrazole

To a solution of 0.2 g sodium in 30 ml ethanol was first added 1.1 g of 5-[3-(2-quinolylmethyloxy)phenyl]-tetrazole and then 30 minutes 0.6 g of ethylbromoacetate and stirring was continued at 80° C. for 16 hours.

Solvent was then removed, diluted with water, filtered, washed with ether, dried giving 0.9 g of crude product which was crystallized by ethylacetate hexane to give 0.6 g product, m.p. 111°–113° C.

EXAMPLE 11

2-[3-(2-Tetrahydrofuranooxymethyl)phenoxymethyl]-quinoline 0.88 g (0.01 mol) of 3-hydroxytetrahydrofuran was dissolved in 50 ml THF to this solution 0.46 g (0.01 mol, 50% oil dispersion) NaH was added slowly over 10 min. To the stirred mixture, 2.8 g (0.01 mol) 2-(3chloromethylphenoxymethyl)quinoline was added slowly. After the addition was completed, the mixture was heated at 70° C. bath temperature for 5 hours. Reaction mixture was concentrated to dryness and slurried into water, and extracted with methylene chloride. The methylene chloride extract was washed with water, dried over MgSO₄ and concentrated to dryness under reduced pressure to obtain oil. The product was passed through a silica gel column using hexane/ethyl acetate (3:1) as eluent. Evaporation of eluent gave orange oil (1.2 g).

EXAMPLE 12

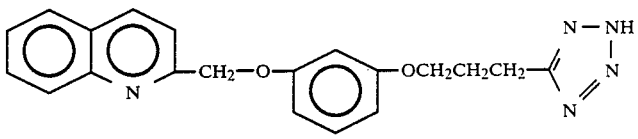

5-[3-(3-(2-Quinolylmethyloxy)phenoxy)propyl]tetrazole

A mixture of 4.4 g of 2-[3-(3-cyanopropoxy)phenoxymethyl]quinoline, 2.6 g of sodium azide and 2.1 g of ammonium chloride in 35 ml of dry dimethylformamide was heated at 140° C. for 18 hours. The reaction mixture was poured onto ice. A solution of 20 ml of 1N sodium hydroxide was added and the solution was extracted twice with ethyl acetate. Concentrated hydrochloric acid was added to acidify the aqueous portion. This was extracted twice with ethyl acetate, dried and evapo-

EXAMPLE 13

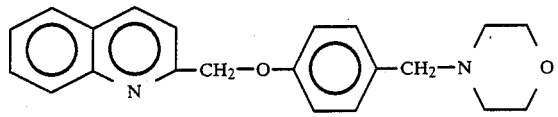

2-(4-(N-Morpholinomethyl)phenyloxymethyl)quinoline

A mixture of 3.6 g (0.18 mol) 4-(N-morpholinomethyl)phenol, 4.0(0.18 mol) 2-chloromethylquinoline hydrochloride and 18 ml (2N, NaOH) in 25 ml DMF and 25 ml THF was heated over a steam bath for a period of 24 hours. The reaction mixture was poured into water and extracted with ether. The ether extract was washed with water, dried over MgSO$_4$ and concentrated to dryness under reduced pressure. The residue was passed through a silica gel column using hexane/ethyl acetate (3:1) as eluent. Evaporation of eluent gave solid (0.8 g) m.p. 92°–93° C.

EXAMPLE 14

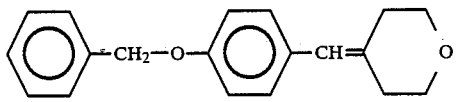

4-(4'-Benzyloxybenzylidine)tetrahydropyran

To a solution of 25 g (0.05 mol) 4-benzyloxybenzyltriphenylphosphonium chloride in 50 ml dry THF, 31.2 ml (0.05 mol) n-butyllithium in hexane was added over a period of 10 minutes. To the stirred mixture, 5 g (0.05 mol) tetrahydro-4H-pyran-4-one was added dropwise. After the addition was completed, the mixture was stirred at room temperature for a period for 2 hours. The reaction mixture was filtered and mother liquor was poured into water and extracted with ether. The ether extract was washed with water, dried over MgSO$_4$ and concentrated to dryness under reduced pressure. The residue was passed through a silica gel column using hexane/ethyl acetate (3:1) as eluent. Evaporation of eluent gave solid (6 g) m.p. 72°–73° C.

EXAMPLE 15

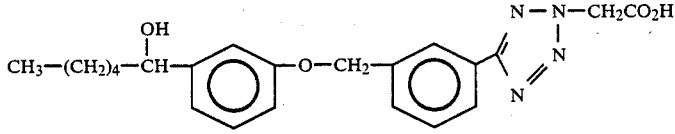

5[3-[3-(1-Hydroxyhexyl)phenoxymethyl]phenyl]2H-tetrazole rated to give 4.5 g of a tan solid. Recrystallization from ethyl acetate gave 1.5 g of pure product of m.p. 147°–149° C.

To 1.5 g of 5[3-[3-(1-hydroxyhexyl)phenoxymethyl]phenyl]2-carbethoxymethyl-2H-tetrazole in 5 ml of methanol was added 6.0 ml of 2N sodium hydroxide. The mixture was stirred for 3 hours. The mixture was acidified with hydrochloric acid and extracted with ether. On evaporation of the ether layer there was obtained 1.3 g of crude product. This was passed through a silica gel column and eluted with chloroform:methanol (4:1) to give 0.9 g of product as a light amber liquid.

EXAMPLE 16

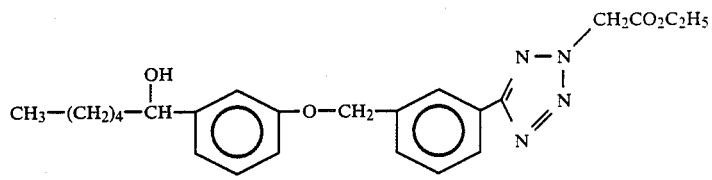

5-[3-[3-(1-Hydroxyhexyl)phenoxymethyl]phenyl]-2-carbethoxymethyl-2H-tetrazole

To a solution of 0.3 g of sodium in 60 ml of ethanol was added 4.3 g of 5[3-[3-(1-hydroxyhexyl)phenoxymethyl]phenyl]-2H-tetrazole and 2.0 g of ethyl bromoacetate. The mixture was refluxed for 18 hours. The solvent was evaporated and the residue was partitioned between ether and water. The ether layer was dried and evaporated to give 4.5 g of a viscous oil. This was passed through a short silica gel column and eluted with chloroform:methanol (4:1). The product (2.3 g) was obtained as a light amber oil.

EXAMPLE 17

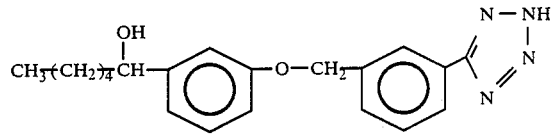

5-[3-[3-(1-Hydroxyhexyl)phenoxymethyl]phenyl]2H-tetrazole

A mixture of 7.2 g of 3-(3-cyano)benzyloxy-1-(1-hydroxyhexyl)benzene, 2.0 g of sodium azide and 1.6 g of ammonium chloride was heated in 90 ml of dry dimethylformamide for 22 hours. The reaction mixture was poured into ice and concentrated hydrochloric acid. The gummy residue was dissolved in ethyl acetate, washed with water, dried and evaporated to give 9.0 g of crude product. This was chromatographed using chloroform:methanol (85:15) as eluent. The crystalline product was slurried with ether and hexane and filtered to give 2.2 g of product, m.p. 81°–83° C.

EXAMPLE 18

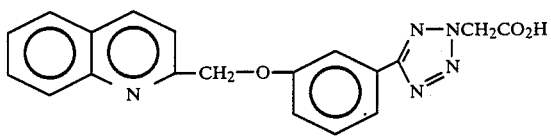

2-Carboxymethyl-5-[3-(2-quinolylmethoyloxy)phenyl]-tetrazole

A mixture of 1.3 g of 2-carbethoxymethyl-5-[3-(2-quinolylmethyloxy)phenyl]tetrazole in 5 ml ethanol and 40 ml of 1N NaOH was stirred at 70° C. for 4 hours. It was cooled, diluted with water, acidified with acetic acid, filtered, washed with water, and then ethyl acetate to give 1.0 g product.

EXAMPLE 19

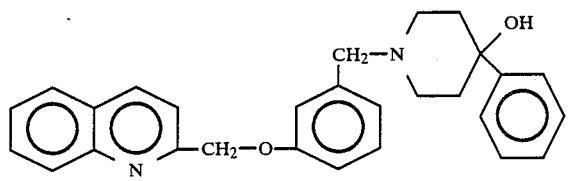

2-[3-(4-Hydroxy-4-phenylpiperidin-1-ylmethyl)phenoxymethyl]quinoline

A mixture of 3.2 g (0.01 mol) 2-(3-chloromethylphenoxymethyl)quinoline hydrochloride, 1.7 g (0.01 mol) 4-hydroxy-4-phenylpiperidine and 1.2 g (0.02 mol) KOH in 5 ml of H2O and 50 ml ethanol was heated over steam bath for a period of 3 hours. Reaction mixture was concentrated to dryness and slurried into water, and extracted with methylene chloride. The methylene chloride extract dried over MgSO4 and concentrated to dryness under reduced pressure to obtain solid. Repeated recrystallization from isopropanol and acetronitrite gave desired product 2 g, m.p. 123°–225° C.

EXAMPLE 20

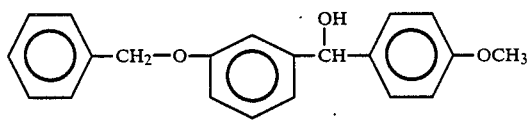

1-(3-Benzyloxyphenyl)-1-(4-methoxyphenyl)methanol

To a solution of 4-methoxyphenyl magnesium bromide in 25 ml THF [prepared from 9.3 g (0.05 mol) of 4-bromoanisole, 1.2 g (0.05 mol) magnesium turnings and 25 ml dry THF] is added 10.6 g (0.05 mol) of 3-benzyloxybenzylaldehyde dissolved in 25 ml THF, over a period of 1 hour. After the addition has been completed, the reaction mixture was allowed to reflux for 112 hours. The mixture was allowed to cool and then hydrolyzed with saturated NH4Cl. Add ether and extract with water, dried over MgSO4 and concentrated to dryness under reduced pressure. The residue was passed through a silica gel column using hexane/ethylacetate (9:1) as eluent. Evaporation of eluent gave 9.7 g solid, m.p. 50°–60° C.

EXAMPLE 21

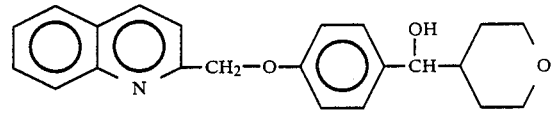

1-(4-Tetrahydropyrano)-1-[4-(2-quinolinylmethoxy)-phenyl]methanol

A mixture of 2.8 g (0.014 mol) 1-(4-tetrahydropyrano)-1-(4-hydroxyphenyl)methanol, 2.9 g (0.014 mol) 2-chloromethylquinoline hydrochloride and 2 g (0.036 mol) KOH in 5 ml water and 50 ml ethanol was heated over steam bath for a period of 3 hours. Reaction mixture was concentrated to dryness and slurried into water and extracted with methylene chloride. The methylene chloride extract was washed with water, dried over MgSO4 and concentrated under reduced pressure to obtain solid. The product was passed through a silica gel column using hexane/ethyl acetate (55:45) as eluent. Evaporation of eluent gave 1.9 g of solid, m.p. 132°–135° C.

EXAMPLE 22

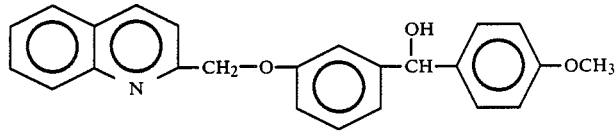

1-(4-Methoxyphenyl)-1-[3-(2-quinolinylmethoxy)-phenyl]methanol

A mixture of 3.7 g (0.016 mol) 1-(3-hydroxyphenyl)-1-(4-methoxyphenyl)methanol, 3.4 g (0.016 mol) 2-chloromethylquinoline hydrochloride and 2 g (0.036 mol) KOH in 5 ml water and 50 ml ethanol was heated over steam bath for a period of 4 hours. Reaction mixture was concentrated to dryness and slurried into water and extracted with methylene chloride. The methylene chloride extract was washed with water, dried over MgSO4 and concentrated to dryness under reduced pressure to obtain oily material. Repeated recrystallization from ethyl acetate, acetonitrite and isopropanol gave desired produce 1.1 g. m.p. 70°–80° C.

EXAMPLE 23

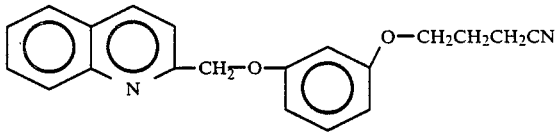

4-(3-(2-Quinolylmethyloxy)phenoxy)butyronitrile

A mixture of 15.3 g of 2-chloromethylquinoline hydrochloride, 12.6 g of 4-(3-hydroxyphenoxy)butyronitrile and 5.7 g of sodium hydroxide was stirred with 80 ml of dimethylsulfoxide at room temperature for 4 hours. The reaction mixture was partitioned between water and ether. The ether extract was evaporated to yield 23.9 g, of crude product. Crystallization from ethyl acetate:hexane and then from ethanol:hexane gave 15 g of grey needles, m.p. 84°–85° C.

EXAMPLE 24

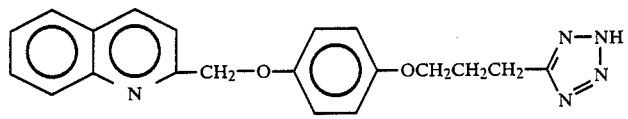

5-[3-(4-(2-Quinolylmethyloxy)phenoxy)propyl]tetrazole

A mixture of 8.0 g of 4-[4-(2-quinolylmethyloxy)phenoxy]butyronitrile, 4.9 g of sodium azide and 4.0 g of ammonium chloride was heated with 25 ml of dry dimethylformamide at 140° C. for 20 hours. The reaction mixture was poured into ice, basified in 1N sodium hydroxide and extracted 2 times with warm ethyl acetate. The aqueous fraction was acidified with acetic acid. The product was filtered and washed with water to give 6.6 g of crude product. Crystallization from ethyl acetate gave 4.2 g of the light tan product, m.p. 158°–160° C.

EXAMPLE 25

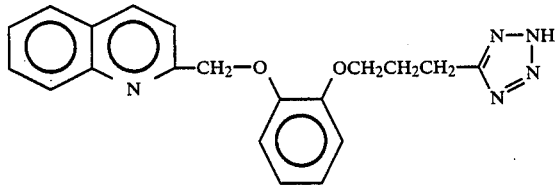

5-[3-(2-(2-Quinolylmethyloxy)phenoxy)propyl]tetrazole

A mixture of 8.7 g of 4-[2-(2-quinolylmethyloxy)phenoxy]butyronitrile, 5.3 g of sodium azide and 4.4 g of ammonium chloride was heated with 25 ml of dry dimethylformamide at 140° C. for twenty hours. The reaction mixture was poured onto ice, basified with 1N sodium hydroxide and extracted 2 times with ethyl acetate. The aqueous fraction was acidified with acetic acid. The product was filtered and washed with water. The crude product was crystallized from acetonitrile to give 1.7 g of pure product of m.p. 137°–140° C.

EXAMPLE 26

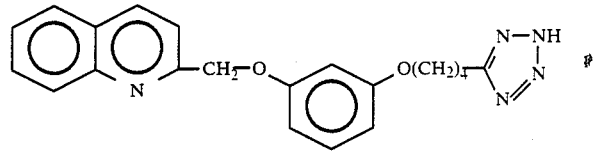

5-[4-(3-(2-Quinolylmethyloxy)phenoxy)butyl]tetrazole nitrile, 5.2 g of sodium azide and 4.3 g of ammonium chloride was heated with 70 ml of dimethylformamide at 140° C. for 20 hours. The reaction mixture was poured onto ice, basified with 1N sodium hydroxide and extracted 2 times with ethyl acetate. The aqueous fraction was acidified with acetic acid and extracted 2 times with ethyl acetate. Evaporation gave 5.6 g of product which was crystallized from ethyl acetate to give 4.4 g of pure product of m.p. 120°–130° C.

EXAMPLE 27

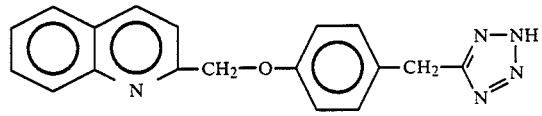

5-[4-(2-Quinolylmethyloxy)benzyl]tetrazole

A mixture of 8.6 g of 4(2-quinolylmethyloxy)phenylacetonitrile, 6.1 g of sodium azide and 5.0 g of ammonium chloride was heated with 70 ml of dry dimethylformamide at 140° C. for twenty hours. The reaction mixture was poured onto ice, basified with 1N sodium hydroxide and extracted 2 times with ethyl acetate. The aqueous fraction was extracted 2 times with ethyl acetate. Removal of solvent left 10.3 g of crude product. This was crystallized from methanol:ethyl acetate to yield 3.3 g of pure product of m.p. 173°–175° C.

In a similar fashion according to the procedures of the preceding examples, the following compounds can be prepared from appropriate starting materials:
2-phenoxymethyl pyridine;
2-phenoxymethyl furan;
2-phenoxymethyl oxazole;
1-phenoxymethyl isoquinoline;
2-phenoxymethyl indole;
2-phenoxymethyl benzoxazole;
2-phenoxymethyl thiophene;
2-phenylthiomethyl quinoline;
1-phenylthiomethyl isoquinoline;
2-phenylthiomethyl furan;
2-phenylthiomethyl indole;
2-phenylthiomethyl thiophene;
2-phenylaminomethyl pyridine;
2-phenylaminomethyl quinoline;
1-phenylaminomethyl isoquinoline;

2-phenylaminomethyl indole;
2-phenylaminomethyl thiophene;
3-phenoxymethyl quinoline;
3-phenoxyethyl quinoline;
3-phenoxymethyl isoquinoline;
2-(2-pyridyloxymethyl)quinoline;
1-(2-imidazolyloxyethyl)isoquinoline;
2-(3-pyrrolyloxymethyl)quinoline;
2-(2-indoloxymethyl)quinoline;
2-(2-naphthyloxymethyl)quinoline;
2-(2-naphthyloxymethyl)quinoline;
2-(2-thienyloxymethyl)quinoline;
2-(2-furyloxymethyl)quinoline;
2-(2-(benzyloxyphenyl)quinoline;
-phenoxymethylnaphthalene;
p-phenylthiomethyltoluene;
-phenylthioethylnaphthalene;
p-phenylaminomethylphenol;
-phenylaminopropylanphthalene;
p-(2-pyridyloxymethyl)anisole;
-(2-imidazolyloxymethyl)naphthalene;
2-phenylpropyloxythiophene;
2-benzyloxyfuran;
2-benzyloxypyridine;
4-phenoxymethylquinoline;
4-phenoxymethylisoquinoline;
8-phenoxyquinoline;
8-benzyloxyquinoline;
2-(2-quinolylmethyloxymethyl)quinoline;
2-(2-pyridylmethyloxymethyl)quinoline;
1-(2-quinolylmethyloxymethyl)isoquinoline;
2-(3-carboxyphenoxymethyl)quinoline;
2-(3-cyanophenoxymethyl)quinoline;
2-(4-fluorophenoxymethyl)quinoline;
2-(3-trifluoromethylphenoxymethyl)quinoline;
2-(4-butoxyphenoxymethyl)quinoline;
6-methoxy-2-(4-fluorophenoxymethyl)quinoline;
8-methoxy-2-(3-trifluoromethylphenoxymethyl)quinoline;
1-(3-butoxyphenoxymethyl)isoquinoline;
1-(3-butylphenoxymethyl)isoquinoline;
6-propionyloxy-2-(3-carboxyphenoxymethyl)quinoline;
8-propionyloxy-2-(3-butoxyphenoxymethyl)quinoline;
6-carbethoxyisopropoxy-2-(3-carboxyphenoxymethyl)quinoline;
8-carbethoxyisopropoxy-2-(3-carboxyphenoxymethyl)quinoline;
2-(3-carboethoxyphenoxymethyl)quinoline
2-(3-carboxyphenoxymethyl)quinoline
2-(3-cyanophenoxymethyl)quinoline
1-(3-trifluoromethylphenoxymethyl)isoquinoline
1-(3-fluorophenoxymethyl)isoquinoline
2-(3-chlorophenoxymethyl)isoquinoline
2-(3-butoxyphenoxymethyl)isoquinoline
2-(m-tolyloxymethyl)quinoline;
2-(3-benzyloxy)methyl)quinoline;
2-(4-phenoxyphenoxymethyl)quinoline;
2-(3,5-dichlorophenoxymethyl)quinoline;
2-(3,4-dimethoxyphenoxymethyl)quinoline;
2-(4-fluorophenoxymethyl)-6-methoxyquinoline;
2-(3-butoxyphenoxymethyl)-6-methoxyquinoline;
2-(4-fluorophenoxymethyl)-8-methoxyquinoline;
2-(3-carboxyphenoxymethyl)-8-methoxyquinoline;
2-(3-carboxyphenoxymethyl)-6-methoxyquinoline;
2-(3-trifluoromethylphenoxymethyl-7-methoxyquinoline;
2-(3-chlorophenoxymethyl)-6-methoxyquinoline;
8-(3-n-butoxy)benzyloxyquinoline;

1-(3-n-butoxyphenoxymethyl)isoquinoline;
2-(3-trifluorophenoxy)-6-methoxyquinoline;
2-(3-carboxyphenoxy)-7-methoxyquinoline;
8-(3-n-butylbenzyloxy)quinoline;
1-(3-carboxyphenoxymethyl)isoquinoline;
2-(4-(4-tetrahydropyranylmethyl)phenoxymethyl)quinoline;
5-(2-[3-(2-quinolylmethyloxy)phenyl]ethyl)tetrazole;
5-(3-[3-(2-quinolylmethyloxy)phenyl]propyl)tetrazole;
5-(2-[3-(2-quinolylmethyloxy)benzyloxy]ethyl)tetrazole;
5-(2-[3-(2-quinolylmethyloxy)phenylethyloxy]ethyl)tetrazole-3-acetic acid;
5-(4-[3-(2-quinolylmethyloxy)phenoxy]butyl)tetrazole;
5-[3-(2-quinolylmethyloxy)phenoxymethyl]tetrazole;
5-(3-[4-(2-quinolylmethyloxy)phenoxy]propyl)tetrazole;
5-(2-[2-(2-quinolylmethyloxy)phenyl]ethyl)tetrazole;
5-(4-[2-(2-quinolylmethyloxy)phenoxy]butyl)tetrazole;
5-(2-[4-(2-quinolylmethyloxy)phenyl]ethyl)tetrazole;
5-(2-[4-(2-quinolylmethyloxy)benzyloxy]ethyl)tetrazole;
5-(2-[4-(2-quinolylmethyloxy)phenylethyloxy]ethyl)tetrazole;
5-[4-(2-quinolylmethyloxy)phenoxymethyl]tetrazole;
5-[2-(2-quinolylmethyloxy)phenoxymethyl]tetrazole;
5-[4-(2-quinolylmethyloxy)phenylmethyl]tetrazole;
5-[2-(2-quinolylmethyloxy)benzyloxymethyl]tetrazole;
5-[2-(3-[(6-methoxy-quinol-2-yl)methyloxy]phenyl)ethyl]tetrazole;
5-(3-[(6-chloro-quinol-2-yl)methyloxy]phenylmethyl)-tetrazole;
5-(3-[(6-carbethoxy-quinol-2-yl)methyloxy]phenoxymethyl)tetrazole;
5-[4-(3-[(6-trifluoromethyl-quinol-2-yl)methyloxy]phenoxy)butyl]tetrazole;
5-[2-(4-[(6-hydroxy-quinol-2-yl)methyloxy]phenoxy)ethyl]tetrazole;
5-(4-[(6-fluoro-quinol-2-yl)methyloxy]benzyloxymethyl)tetrazole;
5-[2-(2-[(6-methoxy-quinol-2-yl)methyloxy]phenyl)ethyl]tetrazole;
5-[3-(2-[(4-methoxy-quinol-2-yl)methyloxy]phenoxy)propyl]tetrazole;
5-[3-(4-[(8-ethoxy-quinol-2-yl)methyloxy]benzyloxy)propyl]tetrazole;
5-(4-[(6-phenoxy-quinol-2-yl)methyloxy]benzyloxymethyl)tetrazole;
5-[3-(3-[(4-acetoxy-quinol-2-yl)methyloxy]phenoxy)propyl]tetrazole;
5-[2-(2-hydroxy-3-[(4-methyl-quinol-2-yl)methyloxy]phenyl)ethyl]tetrazole;
5-(4-[(6-acetomido-quinol-2-yl)methyloxy]phenyl)tetrazole;
5-(3-[(6-methoxy-quinol-2-yl)methyloxy]phenyl)tetrazole;
5-(3-[(6-methoxy-naphth-2-yl)methyloxy]phenoxymethyl)tetrazole;
5-tetrazoloethyl-3-(2-quinolylmethyloxy)benzoate;
2-[3-(p-hydroxyphenoxymethyl)phenoxymethyl]quinoline;
2-[4-(tetrahydrofuranoxymethyl)phenoxymethyl]quinoline;
2-[3-(2-furanoxymethyl)phenoxymethyl]quinoline;
2-[3-(2-furfurylmethyloxy)phenoxymethyl]quinoline;
2-[4-(2-furfurylethyl)phenoxymethyl]quinoline;
2-[4-(4-hydroxycyclohexylmethyl)phenoxymethyl]quinoline;

2-[3-(2-methoxycyclopentylethyl)phenoxymethyl]-quinoline;
2-[3-(N-4-methoxypiperidinomethyl)phenoxymethyl]-quinoline;
2-[3-(2-furfurylmethyloxy)phenoxymethyl]quinoline;
4-[4-(2-quinolylmethyloxy)benzylidine]tetrahydropyran;
8-methoxy-2-[4-(2-oxazolomethyloxy)phenoxymethyl]-quinoline;
6-methoxy-2-[3-(2-thiazolomethyloxy)phenoxymethyl]-quinoline;
8-methoxy-2-[3-(p-hydrophenylmethyl)phenoxymethyl]quinoline;
6-trifluoromethyl-2-[4-(p-methoxyphenylmethyl)-phenoxymethyl]quinoline;
6-chloro-2-[3-(2-thiazolomethyloxy)phenoxymethyl]-quinoline;
6-chloro-2-[3-(2-furanoxymethyl)phenoxymethyl]-quinoline;
4-bromo-2-[4-(4-tetrahydropyranylmethyl)phenoxymethyl]quinoline;
6-chloro-2-[4-(4-tetrahydropyranylmethyl)phenoxymethyl]quinoline;
6-carboxy-2-[3-(2-methoxycyclopentylethyl)phenoxymethyl]quinoline;
8-methoxy-2-[3-(5-tetrazolomethoxy)phenoxymethyl]-quinoline;
4-tetrahydropyranylmethyl-3-(2-quinolylmethyloxy)-benzoate;
5-tetrazolylmethyl-4-(2-quinolylmethyloxy)benzoate;
5-(3-[(6-chloro-quinol-2-yl)methyloxy]phenylmethyl)-tetrazole;
5-[3-(2-quinolylmethyloxy)phenyl]tetrazoloacetic acid;
5-[3-(3-[(6-methoxy-quinol-2-yl)methyloxy]phenoxy)-propyl]tetrazole;
5-[3-(3-[(6-chloro-quinol-2-yl)methyloxy]phenoxy)-propyl]tetrazole;
5-[3-(3-[(8-hydroxy-quinol-2-yl)methyloxy]phenoxy)-propyl]tetrazole;
5-[3-(3-[(4-methylamino-quinol-2-yl)methyloxy]-phenoxy)propyl]tetrazole;
5-[3-(4-[(6-methoxy-quinol-2-yl)methyloxy]phenoxy)-propyl]tetrazole;
5-[3-(4-[(4-methyl-quinol-2-yl)methyloxy]phenoxy)-propyl]tetrazole;
2-[3-(4-[(4-methyl-quinol-2-yl)methyloxy]phenoxy)-propyl]imidazoline;
2-(3-[4-(2-quinolylmethyloxy)phenoxy]propyl)aminoimidazoline;
2-(3-[4-(2-quinolylmethyloxy)phenoxy]propyl)aminoimidazoline;
2-(2-[4-(2-quinolylmethyloxy)phenoxy]ethyl)aminothiozoline;
5-(3-[3-(2-quinolylmethyloxy)phenoxy]propyl)triazine;
5-(2-[3-(2-quinolylmethyloxy)phenoxy]ethyl)aminotriazine;
2-(3-[4-(2-quinolylmethyloxy)phenoxy]propyl)aminooxazoline;
2-(2-[3-(2-quinolylmethyloxy)phenoxy]ethyl)aminooxazole;
Ethyl-4-[3-(2-quinolylmethyloxy)phenoxy]butyrate;
4-[4-(2-quinolylmethyloxy)phenoxy]butyric acid; and
5-[4-(2-pyridylmethyloxy)phenoxypropyl]tetrazole.

The compounds of the present invention have potent activity in regulating lipoxygenase and as such possess therapeutic value in the treatment of inflammatory conditions and allergic responses such as anaphlaxis and asthma.

Lipoxygenases in mammals have been found in the lung, platelets, and white cells. They are enzymes capable of oxidizing arachidonic acid into hydroperoxyeicosatetraenoic acids (HPETEs) and their stable products hydroxyeicosatetraenoic acids (HETEs). Lipoxygenases are classified according to the position in the arachidonic acid which is oxygenated. Platelets metabolize arachidonic acid to 12-HETE, while polymorphonuclear leukocytes contain 5 and 15 lipoxygenases. It is known that 12-HETE and 5, 12-diHETE are chemotactic for human neutrophils and eosinophils, and may augment the inflammation process. 5-HPETE is known to be a precursor of slow-reacting substance of anaphylaxis (SRS-A). The SRS family of molecules, such as leukotrienes C, D, and E have been shown to be potent bronchoconstrictors (see, NATURE 288, 484–486 (1980)).

The following protocol describes an assay to detect inhibitors of the lipoxygenase pathway. Such inhibitors are believed to be capable of modulating the biosynthesis of the leukotrienes, a property believed to be useful in treating asthma and inflammatory disease states.

PROTOCOL FOR DETECTING INHIBITORS OF THE LIPOXYGENASE PATHWAY

A suspension of rat neutrophils in buffer is incubated for 3 minutes at 30° C. with [$^{14}$C]-arachidonic acid (AA) and Calcium Ionophore A23187. Citric acid (2M) is used to quench the reaction. Following the addition of a trace amount of [$^3$H]-5-HETE together with an excess of unlabeled 5-HETE to each tube, the mixture is extracted with chloroform/methanol. The organic layer is washed with dilute acid and an aliquot is transferred to glass tubes and dried. The residue is dissolved in a small volume of chloroform and an aliquot is spotted on silica gel TLC sheets, which are developed with an ethyl acetate/isoctane/water/acetic acid solvent system. The 5-HETE spots are visualized with iodine, cut out and placed in scintillation vials for counting. After adjusting for the extraction efficiency, the amount (pmole) of [$^{14}$C]-5-HETE in each of the tubes is quantiated by subtracting the net pmoles of 5-HETE in the tubes containing buffer alone (blank) from the pmoles of 5-HETE in the tubes containing buffer and cells (control). The ability of the test compounds to modulate the activity of this enzyme is determined by a decrease or increase in the net amount of 5-HETE produced. The results of this test for various compounds of the examples are under the heading 5-LOX-Rat in TABLE I.

PROTOCOL FOR SRS-A (SLOW REACTING SUBSTANCE OF ANAPHYLAXIS) ANTAGONISTS

Leukotrienes, the products of the 5-lipoxygenase pathway of arachidonic acid metabolism, are potent contractile agents with a variety of smooth muscle preparations. Thus, it has been hypothesized that the leukotrienes contribute significantly to the pathophysiology of asthma. This protocol describes an in vitro assay used to test compounds which specifically antagonize the actions of leukotrienes.

Peripheral strips of guinea pig lungs are prepared and hung in tissue baths (Metro #ME-5505, 10 ml) according to the published procedure—(Proc. Nat'l Acad. Sci., U.S.A. Volume 77, pp. 4354–4358, 1980). The strips are thoroughly rinsed in Assay Buffer and then connected with surgical silk thread to support rods from the tissue baths. The rods are adjusted in the baths and the strips connected to the pressure transducers (Grass FT 103 or Gould US-3). The tissue baths are aerated with 95% oxygen—5% carbon dioxide and maintained at 37° C. The assay buffer has been made as follows: for each liter of buffer the following are added to approximately 800 ml of water distilled in glass-6.87 g NaCl, 0.4 g $MgSO_4.7H_2O$, and 2.0 g D-glucose. Then a solution of 0.368 g $CaCl_2.2H_2O$ in.100 ml glass-distilled water is slowly added to the buffer. Sufficient water is added to adjust the volume to one liter, and the solution is aerated with 95% oxygen—5% carbon dioxide. Usually 10 liters of buffer are used for an experiment with 4 tissues.

After the tissues have been repeatedly washed and allowed to equilibrate in the tissue bath, they are challenged with 1 uM histamine. After maximum contractions have been obtained, the tissues are washed, and allowed to relax back to baseline tension. This histamine challenge procedure is repeated at least 1 to 2 more times to obtain a repeatable control response. The average response to 1 uM histamine for each tissue is used to normalize all other challenges.

Responses of each tissue to a predetermined concentration of leukotriene are then obtained. Usually test compounds are examined initially at 30 uM on resting tension of the tissues without any added agonist or antagonist to determine if the compound has any possible intrinsic activity. The tissues are washed and the test compound is added again. Leukotriene is added after the desired pre-incubation time. The intrinsic activity of the compounds, and their effect on leukotriene-induced contractions are then recorded.

The results of this test for some of the compounds of the examples are under the heading SALTI-LTC in TABLE I.

INHIBITIONS OF ($^3$H)-LTD$_4$

Binding Membranes from Guinea Pig Lung

A. Preparation of the Crude Receptor Fraction:

This procedure was adapted from Mong et al. (1984). Male guinea pigs are sacrificed by decapitation and their lungs are quickly removed and placed in a beaker containing ice-cold homogenization buffer. The lungs are separated from connective tissue, minced with scissors, blotted dry and weighed. The tissue is then homogenized in 40 volumes (w/v) of homogenization buffer with a Polytron at a setting of 6 for 30 seconds. The homogenate is centrifuged at 1000×g for 10 minutes (e.g. 3500 RPM, SS-34 Rotor). The supermate is filtered through two layers of cheese cloth and centrifuged at 30,000×g for 30 minutes (e.g. 18,500 RPM SS-34 Rotor), after which the resulting pellet is resuspended in 20 volumes of assay buffer by hand homoginization using a Dounce homogenizer. The final pellet is resuspended in 10 volumes of assay buffer and kept at 4° C. until use.

B. Binding Assay:

Each assay tube (10×100 mm) contains the following:
490 ul Assay Buffer
10 ul Test compound or solvent
100 ul $^3$H-LTD$_4$ (ca. 17,500 DPM)
400 ul Protein preparation Incubations are done at 25° C. for 20 minutes in a shaking water bath. Reactions are started by the addition of the protein preparation. At the end of the incubation time, 4.0 ml of cold wash buffer is added to the tube. After being vortexed, the contents of the tube are immediately poured over a Whatman GF/C filter (25 mm diameter) which is sitting in a vacuum manifold (e.g. Millipore Model No. 3025 manifold) to which a partial vacuum is applied. The filters are immediately washed with an additional 15 ml of cold buffer. The filters are transferred to 7 ml plastic scintillation vials to which 6.0 ml of appropriate scintillation fluid (e.g., Scintiverse) is added. After being allowed to equilibrate for 4–6 hours, the radioactivity is counted with a liquid scintillation counter appropriately set for tritium.

The required control assay tubes include the following:

(a) Total Binding: No test compound is added; buffer is substituted.

(b) Non-Specific Binding: Non-labeled ligand is added at a concentration of 1 uM.

(c) Solvent Controls: If test compound is dissolved in a solvent, controls for both Total Binding and Non-Specific Binding containing solvent but no compounds are required.

The results of this test for some of the compounds of the examples are indicated in Table I under the heading SALTI-I$_{50}$ LTD.

TABLE I

| Example | 5-LOX Rat I$_{50}$ | SALTI-I$_{50}$ LTC | SALTI-I$_{50}$ LTD |
|---|---|---|---|
| 1 | 0.7 | 0.9 | — |
| 2 | 75 | — | — |
| 3 | 0.76 | — | — |
| 4 | 0.15 | 0.5 | 0.5 |
| 5 | 0.45 | 5 | 0.45 |
| 6 | 1.2 | 0.3 | 0.08 |
| 7 | L | 1 | 0.45 |
| 8 | I | 25 | 20 |
| 9 | I | 0.3 | 0.2 |
| 10 | L | 0.3 | 0.36 |
| 11 | 1.3 | 0.6 | — |
| 12 | H | 0.09 | 0.4 |
| 13 | 0.09 | 3 | 5 |
| 21 | H | 2 | 1 |
| 22 | 1.2 | 0.5 | 0.65 |
| 24 | 0.06 | — | — |

What is claimed is:

1. A therapeutic composition comprising an effective anti-hypersensitive amount of a compound of the formula

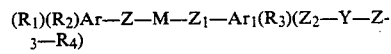

wherein

Ar is quinoline or isoquinoline;

Ar$_1$ is phenyl;

R$_1$, R$_2$, and R$_3$ are independently H, lower alkyl, lower alkoxy, hydroxy, halo, trihalomethyl, hydroxy-lower alkyl, alkyl carboxy, carboxy, formyl, lower alkyl carbonyl, aryl, aryloxy, benzyloxy, lower alkylamino, diloweralkylamino, cyano, lower alkanoyloxy, carbamoyl, lower alkoxy-lower alkoxy, lower carbalkoxy-lower alkoxy, nitro, amino, tetrahydro-pyranylmethyl, or tetrazole, or tetrazole lower alkyl;

R$_4$ is

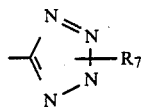

R₇ is H, lower alkyl,

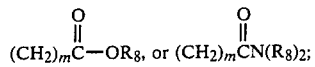

R₈ is H or lower alkyl;
each M is independently O, S, or NR₈;
m is 0 to 5;
n is 0 or 1;
X is O, S, NR₈;
Z, Z₁, Z₂, and Z₃ are independently a chemical bond or an alkylene chain containing up to 5 carbon atoms in the principal chain and up to a total of 8 carbon atoms;
Y is a chemical bond, O, S, NR, CO, CHOR₈, CH=CH, CH₂—CH=CH, COO—, or CH₂;
or a pharmaceutically acceptable salt thereof; and a pharmaceutically acceptable carrier.

2. A method for the treatment of inflammatory or allergic conditions in mammals comprising the administration thereto, in effective anti-inflammatory or anti-allergic doses, of a composition according to claim 1.

3. A method for the treatment of inflammatory or allergic conditions in mammals comprising the administration thereto of an effective therapeutic amount of a compound of the formula

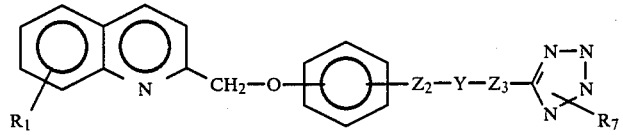

wherein:
R₁ is hydrogen, alkyl having one to about 5 carbon atoms, halo, triflouromethyl, hydroxy, lower alkoxy,

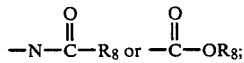

Z₂ and Z₃ are independently a chemical bond or —(CH₂)ₘ—;
Y is a chemical bond, oxy, carbonyl, carboxyl, hydroxymethylene or loweralkoxymethylene;
R₇ is hydrogen, lower alkyl or (CH₂)ₘCO₂R₈;
R₈ is hydrogen or lower alkyl; and
m is 0–5;
or a pharmaceutically acceptable acid addition salt thereof.

4. A compound of the formula

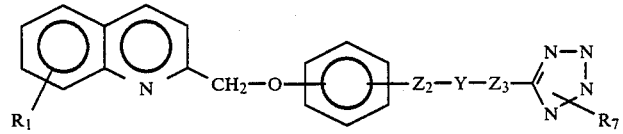

wherein:
R₁ is hydrogen, alkyl having one to about 5 carbon atoms, halo, triflouromethyl, hydroxy, lower alkoxy,

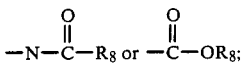

Z₂ and Z₃ are independently a chemical bond or —(CH₂)ₘ—;
Y is a chemical bond, oxy, carbonyl, carboxyl, hydroxymethylene or loweralkoxymethylene;
R₇ is hydrogen, lower alkyl or (CH₂)ₘCO₂R₈;
R₈ is hydrogen or lower alkyl; and
m is 0-5;
or a pharmaceutically acceptable acid addition salt thereof.

5. A pharmaceutical composition for use in treating inflammatory or allergic conditions comprising in admixture with a pharmaceutically acceptable carrier an effective anti-inflammatory or anti-allergic amount of a compound according to claim 4.

6. A compound according to claim 4 wherein Z₂ is a chemical bond and Y is oxy.

7. A compound according to claim 4 wherein Z₂ is a chemical bond and Y is a chemical bond.

8. A compound of the formula

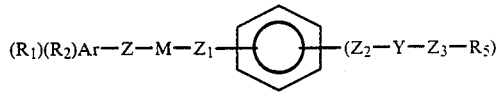

Ar is quinoline or isoquinoline;
R₁ and R₂ are each independently H, lower alkyl, lower alkoxy, hydroxy, halo, trihalomethyl, hydroxy-lower alkyl, carboxy, formly, phenyl, phenoxy, benzyloxy, loweralkylamino, di-loweralkylamino, cyano, lower alkanoyloxy, carbamoyl, lower alkoxy-lower alkoxy, lower carbalkoxy-lower alkoxy, or

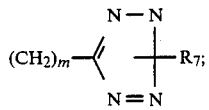

Z, Z₁, Z₂ and Z₃ are independently a chemical bond or an alkylene chain containing up to 5 carbon atoms in the principal chain and up to a total of 8 carbon atoms;

M is O, S, or $NR_8$;

$R_5$ is

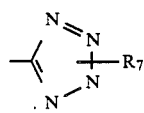

$R_7$ is H, lower alkyl,

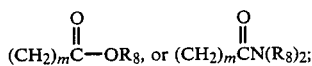

$R_8$ is H or lower alkyl;
each M is independently O, S, or $NR_8$;
m is 0 to 5;
n is 0 to 1;
X is O, S, $NR_8$;
Z, $Z_1$, $Z_2$, and $Z_3$ are independently a chemical bond or an alkylene chain containing up to 5 carbon atoms in the principal chain and up to a total of 8 carbon atoms;
Y is a chemical bond, O, S, NR, CO, $CHOR_8$, CH=CH, $CH_2$—CH=CH, COO—, or $CH_2$;
or a pharmaceutically acceptable salt thereof.

9. A compound according to claim 8 which is 2-carboxymethyl-5-[3-(2-quinolylmethyloxy)phenyl]tetrazole.

10. A compound according to claim 8 which is 5-[3-(4-[2-quinolylmethyloxy]phenoxy)propyl]tetrazole.

11. A compound according to claim 8 which is 5-[3-(2-[2-quinolylmethyloxy]phenoxy)propyl]tetrazole.

12. A compound according to claim 8 which is 5-[4-(3-[2-quinolylmethyloxy]phenoxy)butyl]tetrazole.

13. A compound according to claim 8 which is 5-[4-(2-quinolylmethyloxy)benzyl]tetrazole.

14. A compound of the formula

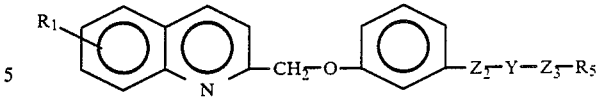

wherein
$R_1$ is H, $C_{1-5}$ alkyl, $OR_8$, halo, $CF_3$,

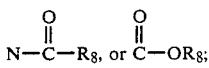

$R_8$ is H or lower alkyl;
$Z_2$ is a chemical bond or $(CH_2)_m$;
$Z_3$ is a chemical bond or $(CH_2)_m$;
m is 0–5;
Y is a chemical bond or

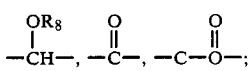

and
$R_5$ is

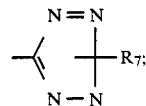

$R_7$ is H, lower alkyl,, or

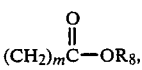

and
n is 0 or 1;
or a pharmaceutically acceptable salt thereof.

15. 5-[3-(2-Quinolylmethoxy)phenyl]tetrazole or a pharmaceutically acceptable salt thereof.

16. 2-Carbethoxymethyl-5-[3-(2-quinolylmethyloxy)phenyl]tetrazole or a pharmaceutically acceptable salt thereof.

17. 5-[3-(3-[2-Quinolylmethyloxy]phenoxy)propyl]tetrazole or a pharmaceutically acceptable salt thereof.

* * * * *